United States Patent
Löw

[19]

[11] Patent Number: 6,027,454
[45] Date of Patent: Feb. 22, 2000

[54] OPHTHALMODYNAMOMETER

[76] Inventor: Bernhard Löw, Poststrasse 19-21, D-66333 Völklingen, Germany

[21] Appl. No.: 08/930,305
[22] PCT Filed: Apr. 18, 1996
[86] PCT No.: PCT/EP96/01627
   § 371 Date: Oct. 21, 1997
   § 102(e) Date: Oct. 21, 1997
[87] PCT Pub. No.: WO96/32884
   PCT Pub. Date: Oct. 24, 1996

[30] Foreign Application Priority Data

Apr. 21, 1995 [DE] Germany .......................... 195 14 796

[51] Int. Cl.[7] ...................................... A61N 5/00
[52] U.S. Cl. ............................ 600/489; 600/481
[58] Field of Search ................... 600/489, 486, 600/561

[56] References Cited

U.S. PATENT DOCUMENTS

| | | |
|---|---|---|
| 3,706,304 | 12/1972 | Sisler ....................................... 600/489 |
| 3,835,836 | 9/1974 | Kanter et al. ........................... 600/489 |
| 3,903,871 | 9/1975 | Chisum et al. ......................... 600/489 |
| 3,929,124 | 12/1975 | Yablonski et al. ...................... 600/489 |
| 4,431,009 | 2/1984 | Marino et al. ........................... 600/486 |
| 4,576,180 | 3/1986 | Taheri ...................................... 600/561 |

FOREIGN PATENT DOCUMENTS

| | | |
|---|---|---|
| 0 114 499 | 8/1984 | European Pat. Off. . |
| 0 327 693 | 8/1989 | European Pat. Off. . |
| 1 035 662 | 8/1953 | France . |
| 10 55 175 | 4/1959 | Germany . |
| 42 35 079 | 4/1994 | Germany . |

*Primary Examiner*—Cary O'Connor
*Assistant Examiner*—Michael Astorino
*Attorney, Agent, or Firm*—Sixbey, Friedman, Leedom & Ferguson; David S. Safran

[57] ABSTRACT

Ophthalmodynamometer (1) with a contact body for applying pressure to an eye (4) to be examined and for increasing the internal ocular pressure, in which the contact body is formed by fundus contact glass (2) which is used to observe the entire ocular fundus and is placed on the eye. Thus, the functions of applying and measuring pressure while simultaneously observing the ocular fundus are combined using the fundus contact glass (2).

9 Claims, 1 Drawing Sheet

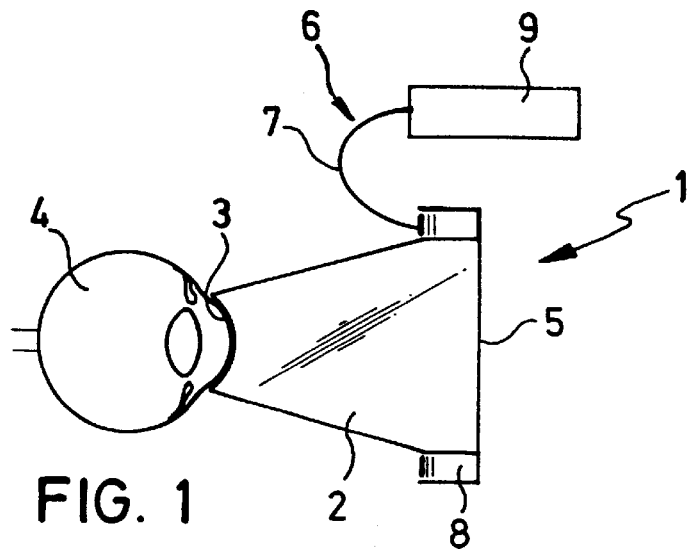
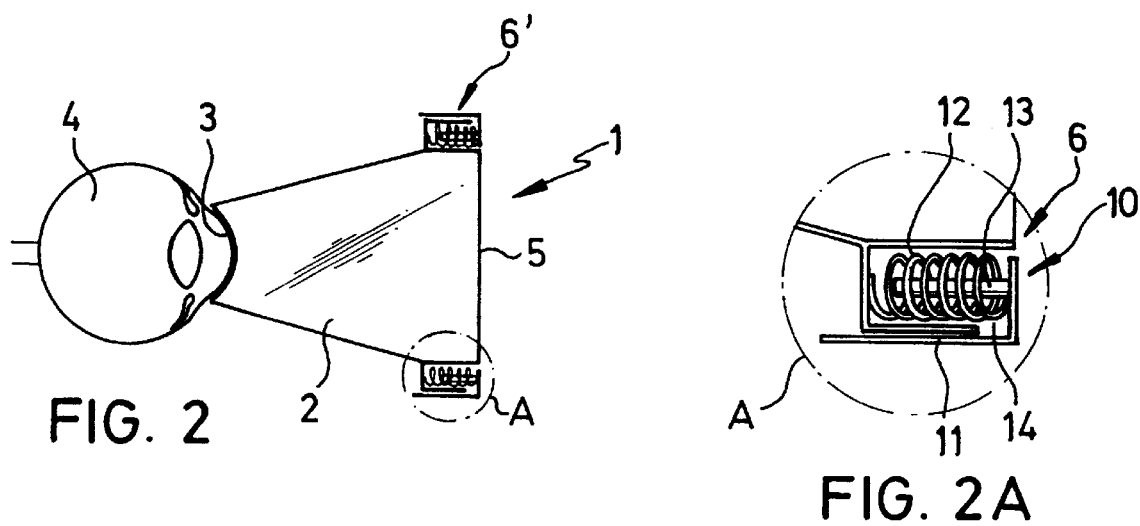
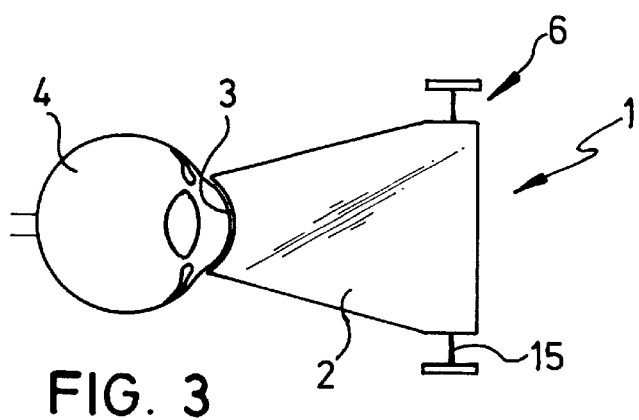

OPHTHALMODYNAMOMETER

BACKGROUND OF THE INVENTION

The invention relates to an ophthalmodynamometer.

Ophthalmodynamometry in medicine is the measurement of the blood pressure on the eye. The blood pressure is measured without bleeding. According to the principle generally known for this purpose, the extravasal tissue pressure is continuously increased until as a result of relief of the vascular wall when the diastolic or minimum blood pressure is exceeded the blood vessel intermittently collapses, and when the systolic or maximum blood pressure is exceeded the blood vessel remains continuously closed. Ophthalmodynamometry is both time-consuming and personnel-intensive since to date at least two specialists were necessary to perform it, of which one operated the instruments for changing the intraocular pressure, and the other observed the vascular pulsations on the ocular fundus by indirect ophthalmoscopy.

FR 1 035 662 or EP 0 327 693 A1 disclose means for performing ophthalmodynamometry which comprise means for pressure generation, such as a contact body for applying pressure to an eye to be examined and for increasing the internal ocular pressure, and pressure detection means. In both publications a separately and specially designed contact body is used. This contact body is made roughly cylindrical; illumination is effected through it using a slit lamp, condenser lens system and partially transparent mirror, and observation optics are assigned for the examination. The hardware of this system is very complex and requires extensive experience when it is used for eye examination. Furthermore, the contact body is made such that light reflection on the surface of the cornea is largely eliminated. Furthermore, examination of the ocular fundus is possible only in the rotationally-symmetrical concave contact areas of the contact body with the cornea of the eye to be examined, so that only the central area of the ocular fundus can be viewed, while the retinal periphery cannot be acquired during the examination. The surface of the contact body away from the eye is flat and provided with an antireflection layer. Furthermore this surface is matched to the optical requirements for illumination and examination of the ocular fundus. The pressure applied via the contact body during ophthalmodynamometry is acquired via an opening closed with a membrane in the center of the cornea via an incompressible fluid as the pressure sensor. Thus the contact body also has a special configuration in that on the one hand it has a membrane and on the other a space which is sealed hermetically tight and which is filled with an incompressible fluid. Thus the pressure detection means is very complex both in terms of design and hardware.

SUMMARY OF THE INVENTION

DE 42 35 079 discloses a device for examining the eye, especially the human eye, which has a measurement probe located in or on a holder which can be placed on the eye. Using an ultrasonic doppler probe or laser probe, functions and states of the eye will be reliably and reproducibly acquired and measured.

In doing so especially the blood flow through the human eye will be acquired, while examination of the ocular fundus and application of pressure to the eye are not addressed.

Conversely, the object of this invention is to make available a ophthalmodynamometer which allows reliable ophthalmodynamometry with minimum hardware and construction cost.

According to the invention an ophthalmodynamometer with a contact body for applying pressure to the eye to be examined and for increasing the internal ocular pressure is made available.

In the ophthalmodynamometer as claimed in the invention a fundus contact glass known in ophthalmology is used; it is used at the same time for application of pressure and as a contact body for increasing the internal ocular pressure and for examining the entire ocular fundus, the detection means for the pressure applied to the fundus contact glass being dynamically connected to the end of the fundus contact glass facing away from the eye. In the ophthalmodynamometer as claimed in the invention therefore the function of observing and studying the entire ocular fundus including the retinal periphery and also the function of a contact body are combined in the fundus contact glass so that neither separate examination optics nor illumination nor a separately configured contact body are necessary. Since furthermore the detection means for the pressure applied to the fundus contact glass is dynamically connected to the end of the fundus contact glass facing away from the eye, in the ophthalmodynamometer according to the invention this detection means does not adversely affect the examination of the ocular fundus using the fundus contact glass.

Thus, using a compact and simple ophthalmodynamometer, ophthalmodynamometry can be reliably performed using extremely simple equipment.

Since in the ophthalmodynamometer as claimed in the invention the pressure on the eye is applied via the fundus contact glass into the underlying cornea, the danger of retinal damage in the application of the pressure is extremely low compared to a contact body with which the sclera with the underlying retina is stretched and flattened by the stamping pressure of the contact body. Thus the ophthalmodynamometer as claimed in the invention can also be operated with considerably reduced risk of injury.

According to the preferred embodiments, the detection means is located on the end of the fundus contact glass away from the eye or it is integrated in the end of the fundus contact glass away from the eye. Thus the pressure applied to the eye can be acquired and read directly on the fundus contact glass. In doing so the existing design of the fundus contact glass can be left unchanged in the area on which the fundus contact glass is placed on the eye to be examined.

According to the invention, it is essential that the pressure be applied with the same means as with the fundus contact glass which is used to observe the ocular fundus, and that the pressure applied to the eye using the fundus contact glass be acquired at the same time in order to be able to assign the vascular pulsations observed on the ocular fundus using the fundus contact glass to the applied pressure values, the pressure exerted on the eye allowing a direct proportional increase of the internal ocular pressure using the fundus contact glass placed on the eye. This yields an operating process which can be easily implemented for an ophthalmodynamometer which furthermore forms a compact unit.

The invention is detailed below using preferred embodiments with reference to the attached drawings.

BRIEF DESCRIPTION OF THE DRAWINGS

FIG. 1 shows a schematic view of a first embodiment of an ophthalmodynamometer,

FIG. 2A–2B show a schematic view of a second embodiment of an ophthalmodynamometer.

FIG. 2A shows an enlarged view of the detection means as shown in A of FIG. 2.

FIG. 3 shows a schematic view of a third embodiment of an ophthalmodynamometer.

DETAILED DESCRIPTION OF THE PREFERRED EMBODIMENTS

Using these figures of the drawings the operating process measures which are important as claimed in the invention are explained in conjunction with the explanation of the ophthalmodynamometer. The same or similar parts are provided with the same reference numbers in the figures.

FIG. 1 shows a ophthalmodynamometer labelled 1 throughout. It comprises fundus contact glass 2 which is shown schematically in a side view and which is suitably shaped on front end 3 facing eye 4 such that it can be placed on eye 4 to be examined such that no cilia are pinched. Fundus contact glass 2 is made as shown in a funnel shape. On back end 5 of fundus contact glass 2 away from eye 4 fundus contact glass 2 is handled by an examiner who is not detailed. The examiner operates the ophthalmodynamometer such that fundus contact glass 2 is placed on eye 4. To increase the internal ocular pressure, a pressure is exerted on eye 4 by means of fundus contact glass 2 by the examiner's pressing on back end 5 of fundus contact glass 2. The pressure applied using fundus contact glass 2 is directly proportional to the increase of the internal ocular pressure produced hereby in eye 4. In the embodiment shown in FIG. 1 an detection means labelled 6 throughout is provided for the pressure applied to fundus contact glass 2 and is dynamically connected to back end 5 of fundus contact glass 2. In the embodiment as shown in FIG. 1, detection means 6, such as a membrane manometer which is connected via connecting line 7 shown schematically to space 8 which surrounds fundus contact glass 2 on back end 5 on the outside acquires this applied pressure. The membrane manometer itself which is labeled 9 is shown only schematically.

In this way the pressure applied to fundus contact glass 2 by the examiner is acquired and at the same time flundus contact glass 2 allows observation, for example, of the vascular pulsations on the ocular fundus. Thus the phenomena of the vessels on the ocular fundus which are typical for achieving minimum and maximum blood pressure can be easily observed and recognized using fundus contact glass 2. The increase of the internal ocular pressure is likewise achieved using fundus contact glass 2. Thus, when ophthalmodynamometer 1 is being operated only one examiner can reliably perform ophthalmodynamometry for example in a simplified manner. Ophthalmodynamometer 1 can be easily handled and is simply designed by its comprising essentially one fundus contact glass 2 which on the one hand is used for observing the ocular fundus and on the other for applying pressure to eye 4. At the same time the pressure exerted by the examiner on fundus contact glass 2 is measured and acquired using assigned detection means 6 on fundus contact glass 2.

In the embodiment shown schematically on FIG. 2, in contrast to the embodiment as shown in FIG. 1, an inductive position transducer is shown as detection means 6'. FIG. 2a shows one example of this inductive position transducer in an enlarged view, labelled 10 there. On the back end labelled 5 of fundus contact glass 2 part 11 which can move relatively is shown; it is supported via spring 12 on fundus contact glass 2. Furthermore, there are induction coils 13 in space 14 formed between fundus contact glass 2 and relatively moving part 11. The pressure exerted on fundus contact glass 2 can then be measured and acquired using this inductive position transducer.

In the embodiment shown in FIG. 3 there is detection means 6" for the pressure exerted on fundus contact glass 2 which comprises wire strain gauges 15 which are provided on back end 5 of fundus contact glass 2.

Of course, detection means 6, 6' and 6" shown and explained above using FIGS. 1 through 3 are only preferred embodiments and examples and one skilled in the art can of course easily undertake suitable modifications, and to acquire the pressure exerted on fundus contact glass 2 can choose accordingly suitable means which can be provided in a space-saving manner on fundus contact glass 2 or can be integrated therein. It is important here that fundus contact glass 2 is used on the one hand for applying pressure, and at the same time it also allows detection of the magnitude of the applied pressure in a simple and reliable manner.

It is important in the ophthalmodynamometer that fundus contact glass 2 is used for observation of the fundus of eye 4 and at the same time to apply pressure to eye 4 to increase the internal ocular pressure. Furthermore, fundus contact glass 2 is used at least as a carrier for detection means 6, 6', and 6" for the pressure applied to fundus contact glass 2, in which this detection and measurement which are directly dynamically linked to fundus contact glass 2 when pressure is applied should take place as accurately as possible for detection of the pressure.

I claim:

1. Ophthalmodynamometer with a contact body for applying pressure to an eye to be examined and for increasing internal ocular pressure comprising a contact body formed of fundus contact glass which is usable for observing the entire ocular fundus and which is placeable on the eye, and a detection means for indicating the pressure applied to the fundus contact glass, said detection means being connected to a side of the fundus contact glass which, in use, faces away from the eye.

2. Ophthalmodynamometer as claimed in claim 1, wherein the detection means is located on an end of the fundus contact glass which, in use, faces away from the eye.

3. Ophthalmodynamometer as claimed in claim 1, wherein the detection means is integrated in an end of the fundus contact glass which, in use, faces away from eye (4).

4. Ophthalmodynamometer as claimed in claim 3, wherein the detection means comprises a membrane manometer.

5. Ophthalmodynamometer as claimed in claim 3, wherein the detection means comprises an inductive position transducer.

6. Ophthalmodynamometer as claimed in claim 3, wherein the detection means comprises wire strain gauges.

7. Ophthalmodynamometer as claimed in claim 1, wherein the detection means comprises a membrane manometer.

8. Ophthalmodynamometer as claimed in claim 1, wherein the detection means comprises an inductive position transducer.

9. Ophthalmodynamometer as claimed in claim 1, wherein the detection means comprises wire strain gauges.

* * * * *